(12) United States Patent
Melchiors et al.

(10) Patent No.: US 6,573,346 B1
(45) Date of Patent: Jun. 3, 2003

(54) OLIGOMERIC AND POLYMERIC TELECHELICS

(75) Inventors: Martin Melchiors, Leverkusen (DE); Hartwig Höcker, Aachen (DE); Helmut Keul, Aachen (DE); Dirk Achten, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/652,075

(22) Filed: Aug. 31, 2000

(30) Foreign Application Priority Data

Jul. 7, 1999 (DE) .......................................... 199 42 614
Sep. 7, 1999 (DE) .......................................... 199 42 615

(51) Int. Cl.$^7$ ................................................ C08F 4/00
(52) U.S. Cl. ........................ 526/217; 526/204; 526/220; 526/328.5; 526/340; 526/342; 526/346; 525/267; 525/314
(58) Field of Search ................................. 526/211, 217, 526/220, 227, 236, 303.1, 307.1, 319, 204, 328.5, 340, 342, 346; 525/267, 314

(56) References Cited

U.S. PATENT DOCUMENTS

| | | | | | |
|---|---|---|---|---|---|
| 5,627,248 | A | * | 5/1997 | Koster et al. | 502/159 |
| 5,677,388 | A | * | 10/1997 | Koster et al. | 525/267 |
| 2002/0061988 | A1 | * | 5/2002 | Klaerner et al. | 526/193 |

FOREIGN PATENT DOCUMENTS

| | | |
|---|---|---|
| WO | 97/46593 | 12/1997 |
| WO | 98/31739 | 7/1998 |

OTHER PUBLICATIONS

J. Am. Chem. Soc. (month unavailable) 1996, 118 (46), 11467–11471, XP000960412, Craig. J. Hawker et al "Radical Crossover in Nitroxide Mediated "Living" Free Radical Polymerizations".
Angew. Chem., Int. Ed. Engl. (month unavailable) 1995, 34 (13/14), 1456–1459, XP000960411, Craig J. Hawker, "Architectural Control in Living" Free Radical Polymerizations: Preparation of Star and Graft Polymers.
J. Org. Chem (month unavailable), 1998, 63 (21), 7130–7131, XP000960555, Ullrich Jahn, "Highly Efficient Generation of Radicals from Ester Enolates by the Ferrocenium Ion. Application to Selective.Alpha–Oxygenation and Dimerization Reactions of Esters".
Advance in Polymer Science 81 (month unavailable), 1987, pp. 167–218, J. C. Brosse et al, "Hydroxyl–Terminated Polymers Obtained by Free Radical Polymerization—Synthesis, Characterization, and Applications".
Makromol. Chem. Rapid Commun. (month unavailable) 1982, 3, pp. 127–132, Takayuki Otsu et al, "Role of Initiator–Transfer Agent–Terminator (Iniferter) in Radical Polymerizations: Polymer Design by Organic Disulfides as Iniferters".
Macromolecules (month unavailable) 1995, 25, pp. 1721–1723, Mitsuru Kato et al, "Polymerization of Methyl Methacrylate with the Carbon Tetrachloride/Dichlorotris-(Triphenylphosphine)Ruthenium(II)/Methylaluminum Bis(2,6–di–tert–butylphenoxide) Initiating System: Possibility of Living Radical Polymerization".
Macromolecules (month unavailable) 1995, 28, pp. 7970–7972, Virgil Percec et al, "Living" Radical Polymerization of Styrene Initiated by Arenesulfonyl Chlorides and $Cu^i(bpy)_nC1$.
Macromolecules (month unavailable) 1996, 29, pp. 1070–1072, Tsuyoshi Ando et al, "Living Radical Polymerization of Methyl Methacrylate with Ruthenium Complex: Formation of Polymers with Controlled Molecular Weights and Very Narrow Distributions".
J. Am. Chem. Soc., (month unavailable) 1994, 116, pp. 11185–11186, Craig J. Hawker, "Molecular Weight Control by a "Living" Free Radical Polymerization Process".
Macromolecules (month unavailable) 1995, 28, pp. 2993–2995, Craig J. Hawker et al "Accurate Control of Chain Ends by a Novel "Living" Free–Radical Polymerization Process".

* cited by examiner

Primary Examiner—Tatyana Zalukaeva
(74) Attorney, Agent, or Firm—Joseph C. Gil; Thomas W. Roy

(57) ABSTRACT

The invention relates to a new process for the preparation of functionalized telechelics based on vinyl polyrners, the telechelics prepared in this way and their use in the plastics, fibers or coating sector.

7 Claims, No Drawings

OLIGOMERIC AND POLYMERIC TELECHELICS

FIELD OF THE INVENTION

The present invention relates to a new process for the preparation of telechelics based on vinyl polymers, the telechelics prepared in this way and their use in the plastics, fibers or coatings sector.

Linear oligomers or low molecular weight linear polymers with functional groups on both chain ends are in general called telechelics. A comprehensive overview of the preparation of telechelics is to be found in Adv. Polym. Sci., 1987, 81, 168. They have acquired importance inter alia as additives and as building units (prepolymers) for higher molecular weight copolymers of defined structure (block copolymers, comb polymers, star polymers). An exact bifunctionality is necessary in particular for use of telechelics as building units for copolymers. The most widely known reactions for the preparation of telechelics having an exact functionality of 2 are polyaddition reactions (to give polyurethanes or polyureas), polycondensations (to give polyesters, polycarbonates or polyamides) and ring-opening anionic or cationic polymerizations of heterocyclic monomers (cyclic esters, carbonates, acetals or ethers). Optionally these reactions are performed with termination reagents which contain the desired functional groups.

Telechelic polyacrylates, i.e. linear oligomers of acrylates or low molecular weight acrylate polymers or copolymers with two defined functional end groups which can participate in the crosslinking, chain lengthening and/or coupling reactions conventionally used in coating chemistry, are of great interest for use in the coating industry.

However, these telechelic polyacrylates cannot be prepared by any of the processes described above for the preparation of telechelics.

Various methods are known in polymer chemistry for providing polyvinyl or polyacrylate compounds with functional end groups. Oxidative chain cleavages (with oxygen, ozone and osmium tetroxide or ruthenium tetroxide) proceed non-specifically and/or require double bonds in the polymer chains as the point of the cleavage. An exact bifunctionality can scarcely be achieved in this way.

The same problem occurs in a free radical polymerization. If a content of monomers which carry the desired functional group calculated for a functionality of two is used, a product mixture is obtained which has only an average functionality of two. Bi-functional molecules are present alongside tri-functional and more than trifunctional, monofunctional and also non-functional polymer molecules. This is based on the statistical character of free radical polymerization and on an influence of the various termination reactions which is difficult to control.

If initiators and/or termination reagents which carry the desired functional groups (functionalized diazo compounds, functionalized peroxides or redox initiators) are employed instead of the monomers carrying functional groups, a functionality of 2 is in general not achieved because of the ratio of the competing termination reactions. Disproportionation, recombination and termination cannot be controlled in a targeted manner by initiator radicals or the termination reagent. In so-called "dead end polymerization", a large excess of an initiator having the desired end group is used so that practically every polymer chain is terminated by an initiator molecule and is thus bifunctional. Only very low molecular weights are achieved in this way and the products formed become uneconomically expensive because of the large amounts of initiator.

In the case of telomerization, i.e. the polymerization of vinyl or acrylate monomers in the presence of chain transfer reagents with high chain transfer constants, likewise only low molecular weights are achieved, and the use of this remains limited to a few cases (polymerization in the presence of carbon tetrachloride, dibromomethane or disulfides carrying functional groups). Since disproportionation as a termination reaction between two active chain ends cannot be suppressed entirely, functionalities of the telechelics of less than 2 are found. In the case of halogen compounds at least, subsequent polymer-analogous reaction of the halogen substituents to give the desired functional groups is also necessary.

Telechelic polymethacrylates can be prepared by group transfer polymerization with ketene silyl acetals, the functional end group being formed by conversion of the silyl groups. However, disadvantages here are the high purity requirements on the monomer and solvent and the price and availability of the initiators required, which means that such a process would be applicable only for special applications.

It is known from EP-A 613910 and EP-A 622378 to prepare α,ω-polymethacrylate diols by selective transesterification of the terminal ester group of an α-hydroxy-functional polyalkyl methacrylate. This process has several disadvantages. On the one hand, the α-hydroxy-functional polyalkyl methacrylate is prepared by free radical polymerization in the presence of large amounts of mercaptoethanol, which is associated with a considerable odor nuisance. On the other hand it is a multi-stage, energy- and time-consuming process which comprises distilling off the excess mercaptoethanol and the solvent used, transesterification with an excess of a diol in the presence of a catalyst, removal of the methanol by distillation, washing of the product several times to remove the catalyst and the excess diol and other purification steps. Furthermore, this reaction, remains limited to the exclusive use of alkyl methacrylates, since otherwise the transesterification reaction no longer proceeds sufficiently selectively on the terminal ester group of the chain.

Ring-opening polymerization of unsaturated heterocyclic compounds is also a special case without a wide application and economic potential (cyclic ketene acetals or unsaturated spiroorthocarbonates); such monomers are not available industrially.

None of the methods described so far is therefore suitable for the preparation of the desired telechelic polyacrylates, since either the required functionality is not achieved, the method remains limited to only a few special cases and/or polymer-analogous after-reactions are necessary. A polymerization process which allows a good control of the polymerization and in particular of the end groups of the polymer chains, while being easy to carry out, is needed. Such a process is living free radical polymerization.

Living free radical polymerization is a relatively young method of controlled free radical polymerization. It combines the advantages of a conventional free radical polymerization (simple synthesis process, inexpensive, broad monomer base) with those of a living polymerization (polymers of defined structure/molecular weight and distribution and end group functionality). The aim of precise control of free radical polymerization is achieved here by a reversible chain termination or blocking ("end-capping") after each growth step. The equilibrium concentration of the polymerization-active chain ends is so low here in comparison with the equilibrium concentration of the blocked ("dormant") chain ends that termination and transfer reactions are severely suppressed compared with the growth reaction. Since end-capping proceeds reversibly, all the chain ends remain "living" if no termination reagent is present. This allows control of the molecular weight, a low polymolecularity index and controlled functionalization of the chain ends by termination reagents.

Controlled free radical polymerization using tetraalkylthiuram disulfides is described by Otsu et al. (Makromol. Chem., Rapid Commun. 1982, 3, 127–132). The preparation of telechelics having functional groups capable of a further reaction or crosslinking with functional groups used in coating chemistry is not disclosed.

Atom Transfer Radical Polymerization (ATRP) is a method, in which a transition metal complex compound $ML_x$ abstracts a transferable atom or atomic group X (Cl or Br) from an organic compound RX to form an oxidized complex compound $ML_xX$ and an organic radical R., which adds on to a vinyl monomer Y to form the carbon radical RY. This radical can react with the oxidized complex compound with transfer of X to give RYX and $ML_x$, which can trigger off a new ATRP and therefore another growth step. The polymerization-active species RY. is thus blocked reversibly by the abstractable group X with the aid of the transition metal compound, which renders the redox process possible.

This method is described inter alia by Sawamoto et al (M=Ru, X=Cl; Macromolecules 1995, 28, 1721; Macromolecules 1996, 29, 1070), Percec et al. (M=Cu, RX=arylsulfonyl halide); Macromolecules 1995 28, 7970), Du Pont (M=Co (inter alia), R. from R—N=N—R; WO 95/25765) and in particular by Matyjaszewski et al. (WO 96/30421 and WO 97/18247). In the latter documents, (co)polymers with one or two functional end groups are also described, these end groups being formed in a polymer-analogous manner from the halide end groups which are initially present. However, this method has the disadvantage that for preparation of the desired telechelics, one or more reaction steps are still necessary after the actual polymerization reaction in order to convert the halide groups into the desired functional groups, while other groups, such as the ester groups of the acrylate monomers, must remain untouched. The ATRP process also has the disadvantage that the polymers must be separated from the catalyst system used (Cu, bipyridine) by an expensive purification process. Residues of Cu impair the color and other properties of the polymers obtained.

U.S. Pat. No. 4,581,429 discloses alkoxyamines which are formed by reaction of linear or cyclic nitroxides, such as 2,2,6,6-tetramethylpiperidin-1-oxyl (TEMPO), with organic carbon-based free radicals, and a process for the preparation of vinyl polymers using these initiators. At temperatures >100° C., the C—ON bond can be cleaved reversibly to re-form the C radical ("active species") and the stable nitroxide radical. The equilibrium lies far on the side of the alkoxyamine ("dormant species"). The result of this reaction is a low, stationary, free radical concentration which, in the case of free radical polymerization of vinyl monomers, means that bimolecular termination reactions are kinetically unfavorable compared with the unimolecular growth reaction. Side reactions are thus largely suppressed and a "living" reaction procedure becomes possible for the free radical polymerization. Hydroxy-functional end groups are described by polymer-analogous reductive splitting of the TEMPO end groups with Zn/acetic acid.

The preparation of vinyl polymers by living free radical polymerization ("Stable Free Radical Polymerization", SFRP) on the basis of alkoxyamines is described by Hawker et al. (J. Am. Chem. Soc. 1994, 116, 11185; Macromolecules 1995, 28, 2993) and Georges et al. (Xerox Comp., U.S. Pat. No. 5,322,912, U.S. Pat. No. 5,401,804, U.S. Pat. No. 5,412,047, U.S. Pat. No. 5,449,724, WO 94/11412, WO 95/26987 and WO 95/31484). The carbon radicals are prepared by addition of free radical initiators (peroxides, azo initiators) on to monomers which can be polymerized by free radicals; these free radicals are then captured in situ by TEMPO to give alkoxyamines. These alkoxyamines are the actual initiators, since they are split reversibly into free radicalsat temperature >100° C. and in this way can initiate the polymerization of the monomers metered in. During the polymerization, the number of growing chains (and therefore the molecular weight) is then detennined by the concentration of the alkoxyamine initiators. Compared with ATRP, this polymerization process offers the advantage of the absence of metals, i.e. the expensive step of separating off the Cu catalyst and its reaction products is omitted here. Difunctional telechelics have previously been obtained only by chain-analogous reactions (oxidative splitting off of the TEMPO end group). The synthesis of polyacrylate telechelics, the functional groups of which are capable of a further reaction or crosslinking with the known functional groups coatings chemistry, by using difunctional alkoxyamine initiators has not previously been described.

WO 97/46593. describes the preparation of hydroxytelechelic butadiene polymers by SFRP. The polymerization of butadiene is carried out in the presence of $H_2O_2$ and TEMPO in a polar solvent. $H_2O_2$ reacts as an initiator and as a termination reagent. Oligomers of <3.000 with a polymolecularity index of 1.3–3.4 and OH functionalities of 0.59–1.69 are obtained. The use of functionalized alkoxyarnine initiators and/or acrylate monomers or styrene is not described here.

The use of alkoxyamine initiators which additionally carry functional groups which are capable of a further reaction or crosslinking with the known functional groups coatings chemistry for the preparation of telechelic polyacrylate copolymers is not described in any of the documents or processes of the prior art mentioned.

An object of the present invention is to provide a process for the preparation of telechelics which does not have the disadvantages of the prior art. In particular, a process is sought which allows the preparation of a homo- or copolymer of one or more vinyl monomers, in particular acrylate monomers, and styrene, in a simple manner and to the effect possible in a one reaction step reaction without subsequent purification. The molecular weight should be established in a controlled manner and a low polymolecularity index (polydispersity) and two functional end groups (Y, OH) should be achieved, wherein Y represents a functional group which is reactive with isocyanates, alcohols, carboxylic acids, anhydrides and/or epoxides. The resulting polymer should also have a thermal stability of $\geq 200°$ C. that is adequate for processing.

SUMMARY OF THE INVENTION

The present invention relates to a process for the preparation of telechelics of the formula HO—B'—Q—B" or HO—B'—G—C—B'" having a molecular weight $200<M_n<50.000$, wherein Q is represented by the formula

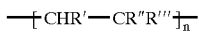

wherein
n is an integer in the range $3 \leq n \leq 500$ and
R', R" and R'" are the same or different and represent H, $C_1$–$C_{20}$-(cyclo)alkyl, $C_6$–$C_{24}$-aryl, halogen, CN, $C_1$–$C_{20}$-cycloalkyl ester or -amide or $C_6$–$C_{24}$-aryl ester or -amide, can also contain further substituents, such as ether groups, and can also be a constituent of a ring structure, in a cyclic anhydride, ester, amide or hydrocarbon, and which comprises reacting
A) monomers A, which can be polymerized by free radicals, of the formula

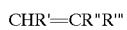

with
B) a functionalized alkox amine initiator B of the formula I:

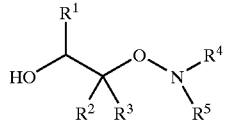

wherein
[—$CR^1$—$CR^2R^3$—] represents B',
$R^1$, $R^2$ and $R^3$ are the same or different and represent H, $C_1$–$C_{20}$-(cyclo)alkyl, $C_6$–$C_{24}$-aryl, halogen, CN, $C_1$–$C_{20}$-(cyclo)alkyl ester or -amide or $C_6$–$C_{24}$-aryl ester or -amide, and
[—O—$NR^4R^5$] represents B"/B'",
$R^4$ and $R^5$ independently of one another represent aliphatic, cycloaliphatic or mixed aliphatic/ aromatic radicals having 1–24 carbon atoms, which can also be part of a 4- to 8-membered ring, wherein the carbon atom of the radicals $R^4$ and $R^5$ directly adjacent to the alkoxyamine nitrogen atom is in each case substituted by 3 further organic substituents (other than hydrogen) or a double-bonded carbon, oxygen, sulfur or nitrogen atom and a further organic substituent (not hydrogen), and
in case of B"
at least one of the radicals $R^4$ and $R^5$ contain a functional group Y,
Y represents a functional group which is reactive with isocyanates, alcohols, carboxylic acids, anhydrides and/or epoxides and
optionally
C) a functionalizing reagent C of the formula $R^{14}R^{15}C=CR^{16}(R^{17}—Y)$,
wherein $R^{17}$ represents a linear or branched, optionally substituted alkyl chain with a minimum length of 1 methylene group and
$R^{14}$, $R^{15}$ and $R^{16}$ independently of one another represent hydrogen or an optionally aryl- or halogen-substituted alkyl radical.

DETAILED DESCRIPTION OF THE INVENTION

The invention also relates to the telechelics HO—B'— Q—B" or HO—B'—Q—C—B'" obtained by this process.

The invention also relates to telechelics prepared from vinyl polymers having a molecular weight $200<M_n<50.000$, afunctionality of 1.5 to 2.0 and a polydispersity (Weight-average molecular weight/Number-average molecular weight) between 1.1 to 1.8. comprising a hydroxyl endgroup and a functional group Y which is reactive with isocyanates, alcohols, carboxylic acids, anhydrides and/or epoxides.

The invention also relates to the use of the telechelics according to the invention as building units for plastics, adhesives or fibers and as binders, binder components or building units for binder components in coating compositions and adhesives.

The process according to the invention comprises two variants which lead to the desired telechelics HO—B'—Q— B" or HO—B'—Q—C—B'".

The polymers obtained by this process carry 2 functional groups incorporated in a terminal position: one chain end is substituted by the OH group of the alkoxyamine initiator [HO—B'—]; the second functional group Y is introduced into the polymer in the terminal position either via the functionalizing reagent C (variant 1, monofunctionalized alkoxyamine initiator [—C—B'".]) or via the alkoxyamine initiator (variant 2, difunctionalized alkoxyamine initiator [—B".]).

The process according to the invention of variant 1 [HO—B'—Q—C—B'"] comprises (co)polymerization or -oligomerization of suitable monomers A by a monofunctionalized alkoxyamine initiator B formula which—apart from its OH group—contains no further functional group Y, followed by an end group functionalization of this polymer by a suitable functionalizing reagent C after complete conversion of the monomers.

Reagent C carries a functional group Y which is reactive with isocyanates, alcohols, carboxylic acids, anhydrides and/or epoxides and can be present during the polymerization or can be added to the batch after substantially complete consumption of the monomers. It terminates the polymer chains carrying a free radical chain end after complete conversion of the monomers and in this way leads to an end group functionalization of the second chain end with the functional group Y.

Y is selected from the group of functional units with the general formulas,

—OH, —CN, —COOH, —COOR[18], —SH, —NHR[18], —OCONHR[19]NCO,

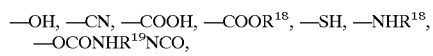

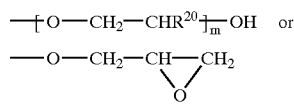

wherein
$R^{16}$ represents hydrogen or a linear or branched $C_1$–$C_6$-alkyl chain and
$R^{18}$ and $R^{19}$ represent any desired $C_1$–$C_{24}$-hydrogen carbon radicals,
$R^{20}$ is hydrogen or any alkyl radical and
m is 1–10

The process according to the invention of variant 2 [HO—B"—Q—B"] comprises the use of difunctionalized alkoxyamine initiators of the formula I, wherein the radicals $R^1$ to $R^5$ have the above-mentioned meaning; however—in contrast to variant 1—these alkoxyamine initiators necessarily contain a functional group Y which is reactive with isocyanates, alcohols, carboxylic acids, anhydrides and/or epoxides. In this variant, a telechelic of the desired structure is obtained without the use of an additional functionalizing reagent C.

According to the invention, all the olefins and substituted olefins which can be polymerized by free radicals and are known from the prior art can be employed with the monomers A. Possible substituents include:

H, linear or branched alkyl radicals having 1–20 carbon atoms, which can optionally also carry further substituents, α,β-unsaturated linear or branched alkenyl or alkinyl radicals, which can optionally also carry further substituents, cycloalkyl radicals, which can also carry heteroatoms, such as O, N or S, in the ring and optionally further substituents, optionally substituted aryl or heteroaryl radicals, halogen, CN, $CF_3$, COOR and COR.

The double bond which can be polymerized by free radicals can also be part of a ring, such as in cyclic olefins or olefinically unsaturated anhydrides, esters, amides or imides.

Monomers which are preferably employed include (meth) acrylic acid esters of $C_1$–$C_{20}$-alcohols, acrylonitrile, cyanoacrylic acid esters of $C_1$–$C_{20}$-alcohols, maleic acid diesters of $C_1$–$C_6$-alcohols, maleic anhydride, vinylpyridines, vinyl(alkylpyrroles), vinyloxazoles, vinyloxazolines, vinylthiazoles, vinylimidazoles, vinylpyrimidines, vinyl ketones, styrene or styrene derivatives which carry a $C_1$–$C_6$-alkyl radical or halogen in the α-position and carry up to 3 further substituents on the aromatic ring.

Butyl acrylate, 2-ethylhexyl acrylate, methyl methacrylate, butyl methacrylate, cyclohexyl methacrylate, isobornyl methacrylate, maleic anhydride or styrene are particularly preferably employed. Any desired mixtures of the above mentioned monomers can also be employed.

Component B is selected from functionalized alkoxyamine initiators of the formula I

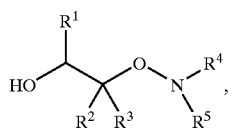

wherein $R^1$, $R^2$, $R^3$, $R^4$ and $R^5$ have the above-mentioned meaning, and wherein at least one of the radicals $R^4$ and $R^5$ can contain a functional group Y which is reactive with isocyanates, alcohols, carboxylic acids, anhydrides and/or epoxides.

Alkoxyamine initiators which are preferably employed are those of the formula IIb:

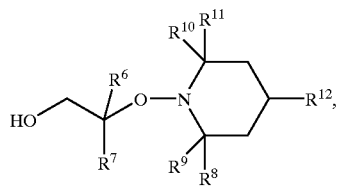

wherein $R^6$=H or $CH_3$, $R^7$ represents an optionally substituted benzene radical or an ester group of the formula —C(=O)OR$^{13}$, $R^{13}$ is a (cyclo)aliphatic alkyl group having 1–20 carbon atoms, $R^8$, $R^9$, $R^{10}$ and $R^{11}$ are the same or different and represent $C_1$–$C_{20}$-(cyclo)alkyl or $C_6$–$C_{24}$-aryl radicals or $C_7$–$C_{24}$-aliphatic/aromatic hydrocarbon radicals, which can additionally contain cyano groups, ether groups, amide groups or OH groups and can also be part of a ring structure, and $R^{12}$ is or contains either hydrogen or a functional group Y which is reactive with isocyanates, alcohols, carboxylic acids, anhydrides and/or epoxides, on the basis of acrylate and methacrylate monomers such as are conventionally used in polyacrylate (co)polymers in coatings technology.

Particularly preferred alkoxyamine initiators are those of the structural formula IIc:

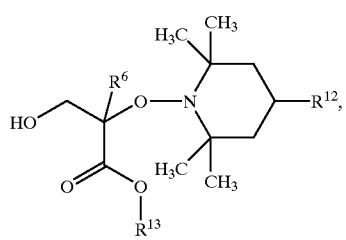

wherein $R^6$=H or $CH_3$, $R^{12}$=H or one of the functional groups OH, $NH_2$ or NHR and $R^{13}$=$CH_3$ or $C_4H_9$.

Whether or not the alkoxyamine initiator B used carries a functional group Y according to the above-mentioned definition depends on which of the two process variants it is employed. In variant 1, alkoxyamine initiators B which are free from functional groups Y according to the above-mentioned definition are used; in variant 2, alkoxyamine initiators B which contain a functional group Y according to the above-mentioned definition in one of the radicals $R^4$, $R^5$ or $R^{12}$ is used.

The functionalizing reagent C is a compound of the formula

$R^{14}R^{15}C=CR^{16}(R^{17}—Y)$, which contains at least one olefinic double bond and at least one functional group Y which is reactive with isocyanates, alcohols, carboxylic acids, anhydrides and/or epoxides, wherein a carbon radical $R^{17}$ which represents a linear or branched, optionally substituted alkyl chain with a minimum length of one methylene group must be present between the double bond and Y, and wherein $R^{14}$, $R^{15}$ and $R^{16}$ independently of one another represent hydrogen or an optionally aryl- or halogen-substituted alkyl radical. Although it is not preferred, a mixture of such compounds can also be employed.

Component C is preferably chosen from the following compounds

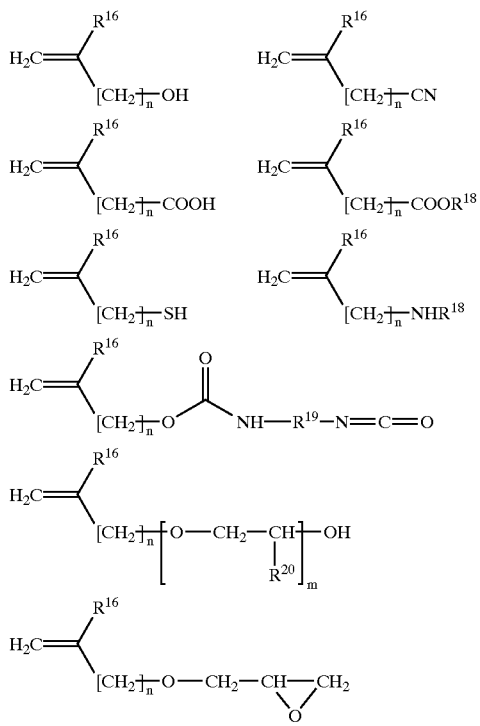

wherein
$R^{16}$ represents hydrogen or a linear or branched $C_1$–$C_6$-alkyl chain,
$R^{18}$ and $R^{19}$ represent $C_1$–$C_{24}$-hydrocarbon radical,
$R^{20}$ is hydrogen or a $C_1$–$C_{24}$-alkyl radical, preferably methyl,
n can be 1—4 and
m can be 1—10.

The use of 2-propen-1-ol, 3-buten-1-ol, 4-penten-1-ol, 5-hexen-1-ol or their propoxylated derivatives obtained by addition of 1–10 mol of propylene oxide on to the OH group is particularly preferred.

Reagent C can be present during the polymerization or can be added to the mixture after substantially complete consumption of the monomers; it terminates the polymer chains carrying a free radical chain end after complete conversion of the monomers and in this way leads to an end group functionalization of the second chain end with the functional group Y.

The determination of the molecular weight of the telechelics by the process according to the invention, the ratio of the components monomer and alkoxyamine initiator and optionally functionalizing reagent has to be controlled according to well know principles in the art.

The ratio of monomer to alkoxyamine initiator depends on the desired molecular weight or degree of polymerization of the telechelic. Since the process according to the invention is a living polymerization which is substantially free from termination or transfer reactions and the functionalizing reagent optionally employed adds on to the active chain ends only after consumption of the monomer (because of its significantly lower rate of reaction with free radicals compared with the monomers), the person skilled in the art can easily calculate the initiator concentration [I] required for a given starting monomer concentration [$M_0$] and desired conversion $x_p$ to achieve the degree of polymerization $P_n$:

$$[I] = x_p * [M]_0 / P_n$$

wherein
$x_p = ([M]_0 - [M])/[M]_0$ represents the conversion and
[M] represents the current monomer concentration at conversion $x_p$. It can be seen from this that telechelics of any desired molecular weight can be prepared by the process according to the invention. Preferably, however, molecular weights of $200 < M_n < 50.000$, particularly preferably molecular weights of $500 < M_n < 10.000$, most preferably molecular weights of $1.000 < Mn < 5.000$ are established. The resulting polymolecularity indices are quite low and in general are in the range $1.1 < M_w/M_n < 1.8$, in most cases in the range $1.2 < M_w/M_n < 1.5$.

If a functionalizing reagent C is used (variant 1), this is employed in an amount which corresponds to a molar ratio of C=C double bonds in the functionalizing reagent C to the alkoxyamine initiator B of at least 1:1, preferably at least 5:1.

The telechelics prepared by the process according to the invention have the general formula HO—B"—Q—B" or HO—B'—Q—C—B''' as previously defined.
wherein Q is represented by the formula

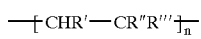

n is an integer in the range $3 \leq n \leq 500$,
R', R" and R''' are the same or different and represent H, $C_1$–$C_{20}$-(cyclo)alkyl, $C_6$–$C_{24}$-aryl, halogen, CN, $C_1$–$C_{20}$-cycloalkyl ester or -amide or $C_6$–$C_{24}$-aryl ester or -amide, can also contain further substituents, such as ether groups, and can also be a constituent of a ring structure, in a cyclic anhydride, ester, amide or hydrocarbon,
wherein [—B'—] is an alkoxyamine fragment [—CR$^1$—CR$^2$R$^3$—],
$R^1$, $R^2$ and $R^3$ are the same or different and represent H, $C_1$–$C_{20}$-(cyclo)alkyl, $C_6$–$C_{24}$-aryl, halogen, CN, $C_1$–$C_{20}$-(cyclo)alkyl ester or -amide or $C_6$–$C_{24}$-aryl ester or -amide, and
wherein B"/B''' is another alkoxyamine fragment of the formula

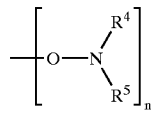

$R^4$ and $R^5$ independently of one another represent aliphatic, cycloaliphatic or mixed aliphatic/aromatic radicals having 1–24 carbon atoms, which can also be part of a 4- to 8-membered ring, wherein the carbon atom of the radicals $R^4$ and $R^5$ directly adjacent to the alkoxyamine nitrogen atom is in each case substituted by 3 further organic substituents (other than hydrogen) or a double-bonded carbon, oxygen, sulfur or nitrogen atom and a further organic substituent (not hydrogen), and
wherein
in case of B"
at least one of the radicals $R^4$ and $R^5$ contain a functional group Y, and
wherein
C) is a functionalizing reagent C of the formula $R^{14}R^{15}C=CR^{16}(R^{17}—Y)$, $R^{14}$, $R^{15}$ and $R^{16}$ independently of one another represent hydrogen or an optionally aryl- or halogen-substituted alkyl radical, and $R^{17}$ represents a linear or branched, optionally substituted alkyl chain with a minimum length of 1 methylene group.

The polymers have functionalities of 1.5 to 2.0; in most cases, however, of >1.8 to 2.0; but never >2.0. One of the two end groups can also be present in derivatized or protected form, functionalities of 0.7 to 1.0; in most cases >0.8 to 1.0 then resulting.

The reaction in the process according to the invention can be carried out at temperatures between room temperature

EXAMPLES

All the data in % are based on the weight.

Preparation of a telechelic according to the invention (table 1):

1 eq alkoxyamine initiator was introduced into a glass flask under a nitrogen atmosphere, and x eq monomer (variants 1 and 2) and optionally y eq functionalizing reagent (variant 1) were added thereto. The mixture was heated to the reaction temperature under nitrogen and stirred at this temperature for t h. After this time, residual monomer and any functionalizing reagent were stripped off in vacuo.

TABLE 1

| Alkoxy-amine initiator | Variant | Time t [h] | Temperature [° C.] | y = eq allyl alcohol | x = eq monomer | Yield [%] | $M_n$ (calc.)[1] | $M_n$ (GPC)[2] | $M_w/M_n$ (GPC)[2] | Functionality[3] a) | b) |
|---|---|---|---|---|---|---|---|---|---|---|---|
| HOST | 1 | 50 | 130 | 5 | styrene 40 | 82 | — | 3,700 | 1.18 | — | 1.2 |
| HOST | 1 | 50 | 130 | 10 | styrene 40 | 81 | — | 3,900 | 1.22 | — | 1.5 |
| HOSTOH | 2 | 4 | 130 | 0 | styrene 40 | 53 | 2,460 | 2,190 | 1.24 | >1.9 | 1.85 |
| HOSTOH | 2 | 3 | 130 | 0 | styrene 20/MA 20 | 51 | 2,110 | 2,140 | 1.28 | >1.9 | >1.9 |
| HOSTOH | 2 | 3 | 130 | 0 | styrene 20/MMA 20 | 38 | 1,660 | 1,990 | 1.43 | 1.8 | >1.9 |
| HOSTOH | 2 | 4 | 130 | 0 | styrene 20/BuA 20 | 56 | 2,760 | 2,720 | 1.31 | 1.9 | 1.8 |
| HOSTOH | 2 | 4 | 130 | 0 | styrene 20/BuMA 20 | 41 | 2,170 | 2,400 | 1.49 | 1.7 | 1.9 |
| HOSTOH | 2 | 4 | 130 | 0 | styrene 20/t-BuA 20 | 52 | 2,540 | 2,420 | 1.23 | 1.9 | 1.8 |
| HOSTOH | 2 | 4 | 130 | 0 | styrene 20/t-BuMA 20 | 37 | 1,930 | 2,080 | 1.47 | 1.8 | >1.9 |
| HOMATOH | 2 | 16 | 130 | 0 | styrene 20/t-BuA 20 | 46 | 2,210 | 2,500 | 1.34 | 1.7 | 1.9 |

Legend to Table 1:
[1]$M_n$ (calc.): Molecular weight calculated from $[M]_0/[I]_0$ and the conversion.
[2]GPC: Eluent THF; polystyrene calibration; $M_n$ and $M_w/M_n$ of the resulting polymers.
[3]Functionality: Determined from $^{31}$P-NMR spectra after functionalization of the polymers with diphenyl chlorophosphate; functionalization based on: a) $M_n$ (calc.); b) $M_n$ (GPC); accuracy in each case ± 0.1.

and 180° C., preferably between 80° and 150° C., particularly preferably between 90° and 130° C. It can be carried out without a solvent (in the monomer or monomer mixture) and also in an organic solvent known in coating technology. It can be carried out in air or in an inert gas atmosphere; an inert gas atmosphere (nitrogen or argon) is preferably used.

The telechelics HO—B'—Q—B" or HO—B'—Q—C—B'" according to the invention can be employed as building units in block copolymers which are contained in plastics, fibers, adhesives or binders or binder components in coating compositions. The functional group Y of the telechelic can be chosen according to the chemical nature of the plastics, fibers, adhesives or binders and the functionalities of the other building units contained therein such that the construction reactions to give the block copolymer proceed readily and in a controlled manner. Via the monomer composition of the central block Q of the telechelic, properties such as hardness, flexibility, hydrophobicity, hydrophilicity, controlled incompatibilities or additional functionalities can be introduced in a controlled manner into the block copolymers prepared therefrom.

The telechelics according to the invention can also be employed in non-modified form, depending on the functionality Y, as binders, binder components, hardeners or hardener components in coating compositions and adhesives.

Monomers used: Styrene, methyl acrylate (MA), methyl methacrylate (MMA), n-butyl acrylate (BA), n-butyl methacrylate (BMA), tert-butyl acrylate (t-BA), tert-butyl methacrylate (t-BMA).

Alkoxyamine initiators used:

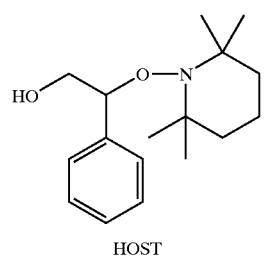

HOST

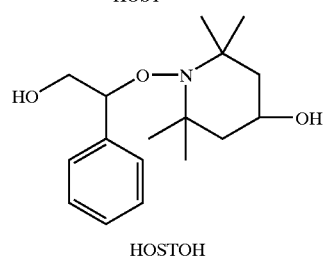

HOSTOH

-continued

HOMATOH

Although the invention has been described in detail in the foregoing for the purpose of illustration, it is to be understood that such detail is solely for that purpose and that variations can be made therein by those skilled in the art without departing fom the spirit and scope of the invention except as it may be limited by the claims.

What is claimed is:

1. A process for the preparation of telechelics corresponding to the formula HO—B'—Q—C—B''' and having a molecular weight $200<M_n<50,000$, wherein Q corresponds to the formula $$-[CHR'-CR''R''']_n-$$

wherein n is an integer in the range of $3 \leq n \leq 500$ and

R', R'' and R''' are the same or different and represent H, $C_1-C_{20}$-(cyclo)alkyl, $C_6-C_{24}$-aryl, halogen, CN, $C_1-C_{20}$-alkyl ester or -amide or $C_6-C_{24}$-aryl ester or -amide, wherein the preceding groups may be substituted or unsubstituted, or the R groups can also be a constituent of a ring structure in a cyclic anhydride, ester, amide or hydrocarbon, which comprises reacting A) a monomer A, which can be polymerized by free radicals and corresponds to the formula

CHR'=CR''R''' with

B) a functionalized alkoxyamine initiator B of the formula I:

wherein

B' represents HO—CR$^1$—CR$^2$R$^3$—,

B'' represents —O—NR$^4$R$^5$,

R$^1$, R$^2$ and R$^3$ are the same or different and represent H, $C_1-C_{20}$-(cyclo)alkyl, $C_6-C_{24}$-aryl, halogen, CN, $C_1-C_{20}$-(cyclo)alkyl-ester or -amide or $C_6-C_{24}$-aryl-ester or -amide, and R$^4$ and R$^5$ are the same or different and represent aliphatic, cycloaliphatic or mixed aliphatic/aromatic radicals having 1–24 carbon atoms, which can also be part of a 4- to 8-membered ring, wherein the carbon atom of the radicals R$^4$ and R$^5$ directly adjacent to the alkoxyamine nitrogen atom is in each case substituted by 3 further organic substituents or a double-bonded carbon, oxygen, sulfur or nitrogen atom and a further organic substituent, and C) a functionalizing reagent C corresponding to the formula

R$^{14}$R$^{15}$C=CR$^{16}$(R$^{17}$—Y), wherein

R$^{17}$ represents a linear or branched, optionally substituted alkyl chain,

R$^{14}$, R$^{15}$ and R$^{16}$ are the same of different and represent hydrogen or an optionally aryl- or halogen-substituted alkyl radical and Y represents a functional group which is reactive with an isocyanate, alcohol, carboxylic acid, anhydride and/or epoxide.

2. The process of claim 1 wherein the reaction is carried out according to the method of "living" free radical polymerization.

3. The process of claim 1 wherein monomer A comprises a member selected from the group consisting of butyl acrylate, 2-ethylhexyl acrylate, methyl methacrylate, butyl methacrylate, cyclohexyl methacrylate, isobornyl methacrylate, maleic anhydride, and styrene.

4. The process of claim 1 wherein 1–5 equivalents of component C, based on component B, are added.

5. The process of claim 1 wherein component C comprises a member selected from the group consisting of the formulas wherein R$^{16}$ represents hydrogen or a linear or branched $C_1-C_6$-alkyl chain, R$^{18}$ and R$^{19}$ represent a $C_1-C_{24}$-hydrocarbon radical, R$^{20}$ and R$^{19}$ represent a $C_1-C_{24}$-hydrocarbon radical, n is 1–4 and m is 1–10.

6. The process of claim 1 wherein component C comprises a member selected from the group consisting of 2-propen-1-ol, 3-buten-1-ol, 4-penten-1-ol, 5-hexen-1-ol, and their propoxylated derivatives obtained by addition of 1–10 mol of propylene oxide on to the respective OH group.

7. The process of claim 1 wherein monomer A comprises a member selected from the group consisting of (meth) acrylic acid esters of $C_1$–$C_{20}$-alcohols, acrylonitrile, cyanoacrylic acid esters of $C_1$–$C_{20}$-alcohols, maleic acid diesters of $C_1$–$C_6$-alcohols, maleic anhydride, vinylpyridines, vinyl(alkylpyrroles), vinyloxazoles, vinyloxazolines, vinylthiazoles, vinylimidazoles, vinylpyrimidines, vinyl ketones, styrene and styrene derivatives substituted with $C_1$–$C_6$-alkyl radical or halogen in the α-position.

\* \* \* \* \*